United States Patent
Yoo et al.

(10) Patent No.: US 7,109,367 B1
(45) Date of Patent: Sep. 19, 2006

(54) (ORGANOTHIOMETHYL)CHLOROSILANES AND THEIR PREPARATION METHODS

(75) Inventors: Bok Ryul Yoo, Seoul (KR); Joon Soo Han, Kyunggi-do (KR); Weon Cheol Lim, Seoul (KR); Mi-Kyoung Hong, Gyeonggi-do (KR)

(73) Assignee: Korea Institute of Science and Technology, (KR)

( * ) Notice: Subject to any disclaimer, the term of this patent is extended or adjusted under 35 U.S.C. 154(b) by 0 days.

(21) Appl. No.: 11/245,786

(22) Filed: Oct. 7, 2005

(30) Foreign Application Priority Data

Mar. 21, 2005 (KR) ...................... 10-2005-0023276

(51) Int. Cl.
*C07F 7/08* (2006.01)
(52) U.S. Cl. ..................................... 556/427
(58) Field of Classification Search ................. 556/427
See application file for complete search history.

(56) References Cited

U.S. PATENT DOCUMENTS

| | | | |
|---|---|---|---|
| 4,613,491 | A | 9/1986 | Jung et al. |
| 6,251,057 | B1 | 6/2001 | Jung et al. |
| 6,392,077 | B1 | 5/2002 | Jung et al. |

FOREIGN PATENT DOCUMENTS

KR    10200000066127  A    11/2000

OTHER PUBLICATIONS

Sorokin et al., *Russian Journal of General Chemistry*, 71(12):1883-90 (2001).
Voronkov et al., *Zhurnal Obshchei Khimii*, 45(8):1807-11 (1975).
Sharipov, *Russian Journal of Applied Chemistry*, 76:108-113 (2003).

*Primary Examiner*—Samuel Barts
(74) *Attorney, Agent, or Firm*—Peter F. Corless; Edwards Angell Palmer & Dodge, LLP

(57) ABSTRACT

This invention relates to (organothiomethyl)chlorosilanes and methods for their preparation by the dehydrohalogenative Si—C coupling reaction of oranothiomethyl halides with Si—H containing chlorosilanes (hydrosilanes), wherein a mixture of oranothiomethyl halide and hydrosilane is heated in the presence of tertiary amine or organic salts (quaternary organoammonium and organophosphonium halides to give (organothiomethyl)chlorosilanes, which is existing a sulfur atom in alkyl chain, (formula: $R^2SCH_2SiCl_2R^1$) in good yield. wherein $R^1$ represents a hydrogen atom, halogen, or $C_1$–$C_6$ alkyl; $R^2$ is selected from the group consisting of $C_1$–$C_6$ alkyl or an aryl group. Especially, this reaction using organic salt as a catalyst provide better economical matter and yield compared with conventional methods, because only catalytic amount of organic salt is required and the catalyst can be separated from the reaction mixture and recycled easily.

10 Claims, No Drawings

(ORGANOTHIOMETHYL)CHLOROSILANES AND THEIR PREPARATION METHODS

CROSS REFERENCE TO RELATED APPLICATIONS

This application is based on, and claims priority from Korean Application No. 2005-0023276, filed on Mar. 21, 2005, the disclosure of which is hereby incorporated by reference.

FIELD OF THE INVENTION

This invention relates to (organothiomethyl)chlorosilanes and methods for their preparation by the dehydrohalogenation Si—C coupling reaction of organothiomethyl halides with Si—H containing chlorosilanes (hydrosilanes), wherein a mixture of organothiomethyl halide and hydrosilane is heated in the presence of tertiary amine or organic salts (quaternary organoammonium and organophosphonium halides to give (organothiomethyl)chlorosilanes, which is existing a sulfur atom in alkyl chain, (formula: $R^2SCH_2SiCl_2R^1$) in good yield. wherein $R^1$ represents a hydrogen atom, halogen, or $C_1$–$C_6$ alkyl; $R^2$ is selected from the group consisting of $C_1$–$C_6$ alkyl or an aryl group. Especially, this reaction using organic salt as a catalyst provide better economical matter and yield compared with conventional methods, because only a catalytic amount of organic salt is required and the catalyst can be separated from the reaction mixture and recycled easily. The (organothiomethyl)chlorosilane compounds can be widely used for the synthesis of various silane monomers, silicone polymers, and surfactants.

BACKGROUND OF THE INVENTION

Organosilicon compounds are important starting materials for organosilicon polymers. Especially, sulfur atom containing organosilicon compounds are interesting and potential monomer precursors in synthesizing functional inorganic polymers. In 1975, Voronkov and co-workers reported that sodium alkylthiolate reacted with haloalkylalkoxysilane to give the corresponding alkylthio-substituted products through the C—S coupling reaction, eliminating sodium halide [Voronkov, M. G.; Sorokin, M. S.; D'yakov, V. M.; Sigalov, M. V. *Zhurnal Obshchei Khimii,* 1975, 45 (8), 1807–11]. Here, 1,1,1-trimethoxy-3-thio-1-silabutane was synthesized by the reaction of methyl iodide with sodium trimethylsilylmethylthiolate [NaSCH$_2$Si(OMe)$_3$].

In 2001, Sorokin; Voronkov reported that a sulfur atom-containing alkylalkoxysilane could be prepared by a Si—C coupling reaction of haloalkylalkoxysilane with RSMgX in tetrahydrofuran in situ [Sorokin, M. S.; Voronkov, M. G. *Russian Journal of General Chemistry,* 2001, 71 (12), 1883–90].

As explained above, the current known methods for preparing sulfur atom-containing organosilanes are limitedly synthesizing alkoxysilanes by S—C coupling of haloalkylalkoxysilane with organometal reagents. However, these methods are not applied for chlorosilane compounds containing Si—Cl bond(s), which can be modified by alcohol, amine, organometal reagents, etc. and haloalkylalkoxysilane should be prepared by two step reactions: hydrosilylation and methoxylations. The former reaction requires a very expensive platinum catalyst and the latter evolves HCl gas in the reaction of Si—Cl with methanol and thus needs a trapping process of HCl.

The inventors have obtained a patent on a method of preparing a variety of organosilicon compounds by the dehydrohalogenation of alkyl halide and chlorosilane in the presence of the tertiary phosphine [U.S. Pat. No. 6,251,057, Korean Patent No. 306574].

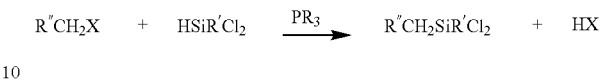

The inventors also prepared organosilicon compounds with Si—Cl bonds from the Si—C coupling reaction of chloromethyl-substituted organosiliocn compounds with chlorosilane containing Si—H bond in better yield using tetraalkylphosphonium salt catalyst instead of tertiary phosphine or amine compound. This tetraalkylphosphonium salt catalyzed reaction provide a better yield compared with phosphine compound-catalyzed reaction, because the catalyst can be separated from the reaction mixture and recycled easily [Jung, I.; Yoo, B.; Han, J.; Kang, S. U.S. Pat. No. 6,392,077].

However, a Si—C coupling reaction of hydrochlorosilane containing Si—H bond with organothiomthyl halide in the presence of organic amine, phosphine, or organic salt have never been reported

SUMMARY OF THE INVENTION

As above-mentioned, the present inventors have discovered that a coupling reaction of organothiomethyl halides and hydrochlorosilanes in the presence of tertiary phosphines, quaternary ammonium salt, or quaternary phosphonium salt as a catalyst proceeded to give the corresponding coupled products, (organothiomethyl)chlorosilicon compounds containing a sulfur atom in organic group, in good yields.

Accordingly, it is an object of the present invention to provide new (organothiomethyl)chlorosilane and methods for their preparation.

DETAILED DESCRIPTION OF THE INVENTION

The present invention relates to (organothiomethyl)chlorosilanes and methods for their preparation by the dehydrohalogenative Si—C coupling reaction of oranothiomethyl halides with hydrosilanes expressed by the following Formula 1 in the presence of quaternary organophosphonium salt catalyst,

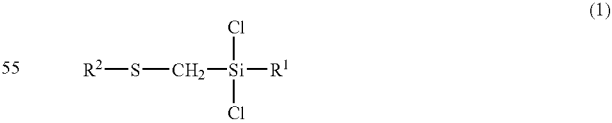

wherein $R^1$ represents a hydrogen atom, halogen, or $C_1$–$C_6$ alkyl; $R^2$ is selected from the group consisting of $C_1$–$C_6$ alkyl or an aryl group.

The present invention relates to (organothiomethyl)chlorosilanes expressed by the following Formula 1 and methods for their preparation by the dehydrohalogenative Si—C coupling reaction of oranothiomethyl halides expressed by the following Formula 3 with hydrosilanes expressed by the following Formula 2 in the presence of quaternary organophosphonium salt, quaternary organoammonium salt, tertiary amine as a catalyst.

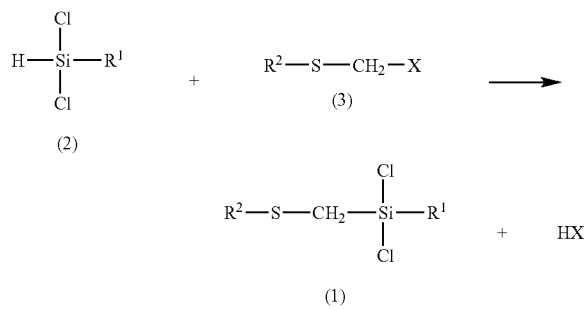

wherein $R^1$, $R^2$, and X are the same as defined above.

The details of the present invention are described as follows.

The present invention relates to preparing new organosilicon compounds having Si—Cl bonds and organic group with a sulfur atom, which can be widely used for the synthesis of various functional organosilicon compounds and silicone monomer, polymers, binders, etc.

In a typical preparation, hydrochlorosilanes expressed by formula II in this invention can be used instead of (haloalkyl)alkoxysilanes used in conventional methods and the reaction is carried out at a lower temperature from 70 to 150° C., preferably 100 to 120° C. than that in the dehydrogenative Si—C coupling of alkyl halide, and further can be applied for a continuous process. The reaction can be carried out using a small amount of quaternary organophosphonium salt or quaternary organoammonium salt as a catalyst. Additionally, the catalyst can be easily recovered from the reaction product and has good catalytic activity for reuse.

The coupling reaction of hydrochlorosilanes expressed by formula II with organothiomethyl halides expressed by formula III in the present invention in the presence of a catalyst of which one among quaternary organophosphinium salt, quaternary organoammonium salt, or organic base can afford organothiomethylchlorosilanes compounds in good yields. In a typical preparation, hydrochlorosilanes of the following formula II, organothiomethyl halides of formula III, and a catalyst are placed all together into a sealed stainless steel tube under inert atmosphere after sealing the reaction tube with a stainless steel stopper. The reaction is carried out at high temperature and under high pressure.

In the coupling reaction explained above, the amount of organothiomethyl halides of formula III is equivalent or more, preferably 1 to 5 folds, relative to the amount of the hydrochlorosilane compounds of formula II. Organic salt or organic base is used as a catalyst in an amount sufficient to catalyze the reaction, generally, 1 to 100 mol %, preferably 3 to 15 mol %, relative to the mole of the hydrochlorosilane compounds of formula II.

In the coupling reaction explained above, the coupling reaction can be carried out in most aliphatic or aromatic hydrocarbon solvents such as hexane, benzene toluene, etc, but also proceeds in neat condition.

In the coupling reaction explained above, the reaction is carried out at a temperature from 70 to 150° C., preferably 100 to 120° C.

In the coupling reaction explained above, the heating and stirring of a reaction mixture may be applied for a certain period of time, generally 1 hr to about 48 hours to complete the reaction. When the reaction is completed, the target compound can be obtained by distilling the reaction mixture under normal or reduced pressure.

The organic salt catalysts such as quaternary organophosphonium salt and quaternary organoammonium salt can be easily recovered from the reaction mixture by two following methods: first, the products are distilled out under atmospheric pressure and vacuum and the remaining catalyst can be washed with aliphatic hydrocarbon solvents and purified by recrystallization. The recovery ratio can be as high as 90%. Second hydrocarbon solvents are added to the product mixture to precipitate out the catalyst and the catalyst is filtered and recovered for recycling. When recovered catalyst is reused for the Si—C coupling reaction, the similar activity is shown in the repeated five runs of coupling reactions.

As mentioned above, even though the recovery ratio can be as high as 90%, when organic phophonium salt immobilized on silicone resins, silica, or zeolite is used the recovery of the catalyst is more convenient and easier for recycling as previously reported (Jung, I. N.; Cho, K. D.; Lim, J, C; Yoo, B. R., U.S. Pat. No. 4,613,491).

The details of starting materials and catalysts used in the Si—C coupling reaction in the present invention are described as follows.

As explained above, hydrochlorosilanes with Si—H bond expressed by formula 2 used in this invention may be dichlorosilane, trichlorosilane, and alkyldichlorosilane.

Organothiomethyl halide, raw material of this invention, expressed by the following Formula 3 may be alkylthiomethyl halide and arylthiomethyl halide Examples of the organothiomethyl halide expressed by Formula 2 are methylthiomethyl chloride and phenylthiomethyl chloride, etc.

The catalyst of this invention expressed by the following Formulae 4, 5 and 6 may be quaternary phosphonium salt, quaternary ammonium salts and tertiary amine.

Quaternary organic salt in this invention can be expressed by the following Formula 4 and 5,

wherein E represents a phosphorus or a nitrogen atom; X may be chloro, bromo or iodo; and R" may be identical or different and is a $C_1$–$C_{12}$ alkyl, phenyl group or —$CnH_{2n+1}$—$C_6H_5$ (n is an integer of 0–6); and two of the R" functional groups may be covalently bonded to form a $C_4$–$C_8$ ring.

wherein E, X and R" are defined as above; and Y can be $C_{1-12}$alkylene or aromatic group optionally containing alkyls.

The organic, salt of the following formula 4 used in this invention may be quaternary organophosphonium halide or quaternary organoammonium halide. Specific examples of the quaternary organophosphonium salt are tetrabutylphosphonium chloride, tetrabutylphosphonium bromide, tetrabutylphosphonium iodide, methyltributylphosphonium chloride, tetramethylphosphonium bromide, tetraethylphosphonium chloride, hexyltriphenylphosphonium chloride, and tetraphenylphosphonium chloride, etc. Specific examples of quaternary organoammonium halide are the same except that nitrogen atom is replaced instead of phosphorous atom of quaternary organophosphonium halide. Specific examples of quaternary organophosphonium salt of the following formula 5 used in this invention may be bis(chlorotrialkylphosphonium)alkylene, bis(chlorotrialkylphosphonium)phenylene, bis(chlorotriphenylphosphonium)alkylene, bis(chlorotriphenylphosphonium)phenylene, and etc. Specific examples of quaternary organoammonium halide of the following formula 5 used in this invention are the same except that nitrogen atom is replaced instead of phosphorous atom of quaternary organophosphonium halide.

Tertiary amine in this invention can be expressed by the following Formula 6

$$(R'')_3N \qquad (6)$$

wherein R" is same as defined above.

The organic base of the following formula 5 used in this invention may be tertiary organic amines.

Specific examples of tertiary amine compounds are trimethylamine, triethylamine, tributylamine, etc.

As explained above, even though organic salt or organic base is used for the Si—C coupling reaction in this invention, organic salt or organic base immobilized on silicone resins, silica, or zeolite can be easier recovery and more convenient for recycling.

As explained above, this method uses a small amount of catalyst, which can be easily recovered for reuse and has good catalytic activity even at low temperature. Considering these advantages, the present invention is a very economical and effective method, which can be used for the preparation of new and various organothiomethylsilicon compounds. Furthermore, its process is very simple and the production cost is relatively low.

Also, the organosilicon compounds, expressed by formula 1, prepared by this invention can be widely used for the synthesis of various polymers and silicone surfactants, because organothiomethyl group of silane can be converted to sulfoxide group applicable to hydrophilic silicones. These compounds are new type hydrophilic silicone different from modified polyethylene- or propyleneoxide-silicones. Generally dialkyl sulfide can be converted to dialkyl sulfonoxide or sulfone by the oxidation reaction with hydrogen peroxide (A. Kh. Sharipov, Russian Journal of Applied Chemistry, 2003, 76, 108–113). Thus oragnothiomethylchlorosilanes may be chemically bonded to inorganic substrate and oxidized to make surface to be hydrophilic.

The invention will be further illustrated by the following examples. However, they should not construed as limiting the scope of the present invention.

EXAMPLE 1

Preparation of (methylthiomethyl)trichlorosilane

A reaction chamber (a 250 mL stainless steel tube) dried in an oven was cooled to room temperature under dry nitrogen gas. methylthiomethyl chloride (138.1 g, 1.02 mol), trichlorosilane (138.1 g, 1.02 mol) and tetrabutylphosphonium chloride (5.01 g, 0.0169 mol) were put in the chamber under nitrogen atmosphere. The opening of the reaction chamber was closed with a cover and the reaction was carried out at 100° C. for 12 hours. This reaction mixture was distilled under normal pressure to give (methylthiomethyl)trichlorosilane (52.2 g, yield: 73.8%).

$^1$H-NMR(CDCl$_3$, ppm) δ2.26(s, 3H, CH$_3$), 2.41(s, 2H, CH$_2$)

EXAMPLE 2

Preparation of methyl(methylthiomethyl)dichlorosilane

As in Example 1, methylthiomethyl chloride (49.2 g, 0.428 mol), methyldichlorosilane (49.2 g, 0.428 mol) and tetrabutylphosphonium chloride (2.10 g, 0.00713 mol) were put in a 250 mL stainless steel tube under nitrogen atmosphere. The reaction chamber was closed with a cover and the reaction was carried out at 100° C. for 12 hours. This reaction mixture was distilled to give 25.04 g of methyl (methylthiomethyl)dichlorosilane in 20.2% yield.

$^1$H-NMR(CDCl$_3$, ppm) δ0.87(s, 3H, SiCH$_3$), 2.27(s, 3H, SCH$_3$), 2.28(s, 2H, CH$_2$)

EXAMPLE 3

Preparation of (phenylthiomethyl)trichlorosilane

As in Example 1, phenylthiomethyl chloride (2.97 g, 0.0187 mol)), trichlorosilane (7.61 g, 0.0562 mol) and tetrabutylphosphonium chloride (2.97 g, 0.0187 mol) were put in a 50 mL stainless steel tube under nitrogen atmosphere. The reaction chamber was closed with a cover and the reaction was carried out at 120° C. for 12 hours. This reaction mixture was distilled under low pressure to give 2.15 g of (phenylthiomethyl)trichlorosilane in 44.5% yield.

$^1$H-NMR(CDCl$_3$, ppm) δ 2.91 (s, 3H, CH$_2$), 7.21–7.42 (m, 5H, ArH)

EXAMPLE 4

Preparation of methyl(phenylthiomethyl)dichlorosilane

As in Example 1, phenylthiomethyl chloride (3.31 g, 0.0209 mol), methyldichlorosilane (7.23 g, 0.0628 mol) and tetrabutylphosphonium chloride (0.615 g, 0.00209 mol) were put in a 50 mL stainless steel tube under nitrogen atmosphere. The reaction chamber was closed with a cover and the reaction was carried out at 120° C. for 12 hours. This reaction mixture was distilled under low pressure to give 1.82 g of methyl(phenylthiomethyl)dichlorosilane in 36.9% yield.

$^1$H NMR(CDCl$_3$, ppm) δ 0.84(s, 3H, SiCH$_3$), 2.71(s, 2H, CH$_2$), 7.19–7.37(m, 5H, ArH)

EXAMPLE 5

Preparation of (methylthiomethyl)trichlorosilane

HSiCl$_3$ + CH$_3$SCH$_2$Cl ⟶ CH$_3$SCH$_2$SiCl$_3$

1) Reaction in the presence of triethylamine

As in Example 1, methylthiomethyl chloride (1.16 g, 0.0120 mol), trichlorosilane (8.13 g, 0.0600 mol) and triethylamine (1.21 g, 0.0120 mol) were put in a 50 mL stainless steel tube under nitrogen atmosphere. The reaction chamber was closed with a cover and the reaction was carried out at 100° C. for 12 hours. This reaction mixture was distilled under low pressure to give 1.12 g of (methylthiomethyl)trichlorosilane in 47.8% yield.

2) Reaction in the presence of tetrabutylammonium chloride

As in Example 1, methylthiomethyl chloride (1.04 g, 0.0108 mol), trichlorosilane (4.39 g, 0.0324 mol) and tetrabutylammonium chloride (0.301 g, 0.00108 mol) were put in a 50 mL stainless steel tube under nitrogen atmosphere. The reaction chamber was closed with a cover and the reaction was carried out at 100° C. for 12 hours. This reaction mixture was distilled under low pressure to give 1.08 g of (methylthiomethyl)trichlorosilane in 51% yield. Having now fully described the present invention, it will be apparent to one of ordinary skill in the art that many changes and modifications can be made thereto without departing from the spirit of scope of the invention as set forth herein.

INDUSTRIAL APPLICABILITY

As explained above, the present invention relates to (organothiomethyl)chlorosilanes with a sulfur-containing alkyl group and their preparation expressed by Formulas 1 by the Si—C coupling reaction of Si—H containing chlorosilanes with organothiomethyl halide in the presence of quaternary organic salt catalyst or amines. Especially, this reaction using organic salt as a catalyst provide better economical matter and yield compared with conventional methods, because only catalytic amount of organic salt is required and the catalyst can be separated from the reaction mixture and recycled easily. Si—H containing silanes used in this invention are an easily available material in the industry. Therefore, this invention is effective for industrial mass production of (organothiomethyl)chlorosilane compounds, which are widely used for raw material of silicon polymers, silicone adhesives, etc.

What is claimed is:

1. (Organothiomethyl)chlorosilane derivatives of the following formula 1,

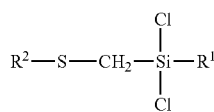   (1)

wherein R$^1$ represents a hydrogen atom, halogen or C$_1$–C$_6$ alkyl; R$^2$ is selected from the group consisting of a C$_1$–C$_6$ alkyl or an aryl group.

2. A process for preparing (organothiomethyl)chlorosilane compounds of the following formula 1, comprising a dehydrohalogenative coupling reaction of hydrochlorosilane of the following formula 2 with organothiomethyl halides of the following formula 3 in the presence of an organic salt (quaternary phosphonium salt or quaternary ammonium salt) or tertiary amine as a catalyst,

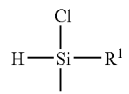   (2)

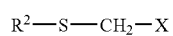   (3)

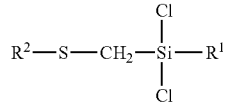   (1)

wherein R$^1$ represents a hydrogen atom, halogen or C$_1$–C$_6$ alkyl; R$^2$ is selected from the group consisting of a C$_1$–C$_6$ alkyl or an aryl group; X represents halogens.

3. A method of preparing (organothiomethyl)chlorosilane compounds according to claim 2, wherein organic salt such as quaternary phosphonium salt or quaternary ammonium salt, expressed by the following Formula 4, is used for said catalyst, (R")$_4$EX   (4)

wherein E represents a phosphorus or nitrogen atom; X represents halogens and R" may be identical or different and is a C$_1$–C$_{12}$ alkyl, phenyl group or —C$_n$H$_{2n+1}$—C$_6$H$_5$ (n is an integer of 0–6); and two of the R" functional groups may be covalently bonded to form a C$_4$–C$_8$ ring.

4. A method of preparing (organothiomethyl)chlorosilane compounds according to claim 2, wherein organic salt such as quaternary phosphonium salt or quaternary ammonium salt, expressed by the following Formula 5, is used for said catalyst,

X(R")$_3$E—Y—E(R")$_3$X   (5)

wherein E, X and R" are the same as defined in claim 3; and Y can be C.sub.1–12 alkylene or aromatic group optionally containing alkyls.

5. A method of preparing (organothiomethyl)chlorosilane compounds according to claim 2, wherein the organic base of the following formula 6 may be tertiary organic amines, (R")$_3$N   (6)

wherein R" is the same as defined in claim 3.

6. A method of preparing (organothiomethyl)chlorosilane compounds according to any one of claims 3, 4, or 5, wherein its immobilized compound on inorganic or organic support is used as catalyst.

7. A method of preparing (organothiomethyl)chlorosilane compounds according to claim 6, wherein said catalyst may be organic salt or base immobilized on a silicon resin, silica, inorganic supporter or organic polymer.

8. A method of preparing (organothiomethyl)chlorosilane compounds according to claim 2, wherein 0.01–1 mol of said catalyst is used for 1 mol of hydrochlorosilane expressed by formula 2.

9. A method of preparing (organothiomethyl)chlorosilane compounds according to claim 2, wherein said coupling reaction is performed in the temperature range of 70–150° C.

10. A method of preparing (organothiomethyl)chlorosilane compounds according to claim 2, wherein said coupling reaction is performed without a reaction solvent.

* * * * *